United States Patent [19]
Ascher et al.

[11] 4,055,646
[45] Oct. 25, 1977

[54] 1-(5-NITROTHIAZOLYL-2)-3-(PIPERAZINOMETHYL)-IMIDAZOLIDINONES-2 AND CORRESPONDING IMINO AND THIONES

[75] Inventors: Gerd Ascher; Hellmuth Reinshagen, both of Vienna, Austria

[73] Assignee: Sandoz Ltd., Basel, Switzerland

[21] Appl. No.: 655,729

[22] Filed: Feb. 6, 1976

[30] Foreign Application Priority Data

Feb. 13, 1975 Switzerland .......................... 1773/75

[51] Int. Cl.$^2$ .................. C07D 417/14; A61K 31/495
[52] U.S. Cl. .............................. 424/250; 260/268 H; 260/293.57; 260/306.8 R; 424/267

[58] Field of Search .................... 260/268 H; 424/250

[56] References Cited
U.S. PATENT DOCUMENTS 3,914,248  10/1975  Ilvespää .......................... 260/268 H Primary Examiner—Donald G. Daus
Assistant Examiner—Jose Tovar
Attorney, Agent, or Firm—Gerald D. Sharkin; Robert S. Honor; Thomas O. McGovern

[57] ABSTRACT

This invention provides novel 5-nitrothiazolo-2-imidazoles which are useful as chemotherapeutical agents.

9 Claims, No Drawings

1-(5-NITROTHIAZOLYL-2)-3-(PIPERAZINOMETHYL)-IMIDAZOLIDINONES-2 AND CORRESPONDING IMINO AND THIONES

This invention provides 5-nitrothiazoloimidazole derivatives of formula I,

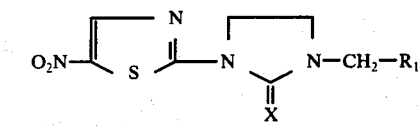

in which
X is oxygen, sulphur or imino, and
$R_1$ is (a) a radical of formula II,

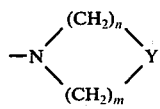

in which
n and m, which may be the same or different, each signifies 2 or 3, and
Y signifies (i) a direct bond or —CH$_2$—, or (ii) an =N-alkly group, in which the alkyl group contains 1 to 4 carbon atoms and is optionally substituted by one or more hydroxy groups, or (iii) a radical of formula III,

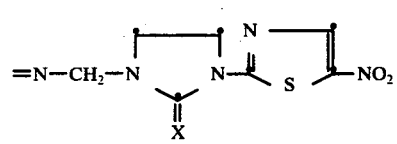

in which X is as defined above, the groups X then being the same, or (iv) a radical of formula IV,

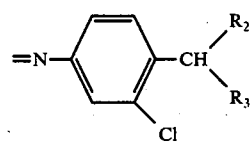

in which either $R_2$ is hydrogen or hydroxy and $R_3$ is hydrogen or $R_2$ and $R_3$ together signify oxygen, or (b) a radical of formula V,

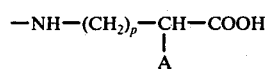

in which
p is 2 or 3, and
A is hydrogen or amino.

The invention also provides a process for the production of compounds of formula I characterised by reacting a compound of formula VI,

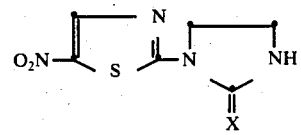

in which X is as defined above,
with a compound of formula VII, $$H—R_1 \qquad \text{VII}$$

in which $R_1$ is as defined above,
and formaldehyde, or the reaction product of a compound of formula VII and formaldehyde.

The process is suitably effected by adding formaldehyde, preferably in the form of paraformaldehyde, to a solution of the compound of formula VII in an inert solvent, for example a cyclic ether, such as dioxane. The mixture is then suitably maintained, for example for 10 to 60 minutes, more usually approximately 30 minutes, at a temperature of from room temperature to the reflux temperature of the reaction mixture, preferably at about 40° C. The compound of formula VI is then suitably added and the mixture maintained, for example for 8 to 30 hours, more usually 10 to 24 hours, for example, at room temperature or an elevated temperature, preferably a temperature of from 40° to 75° C. It will be appreciated that, when a compound of formula Ia,

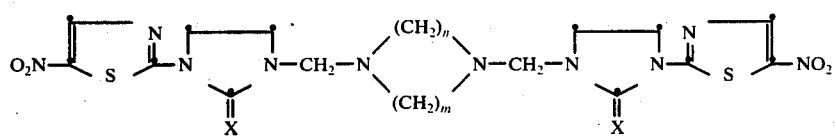

in which n, m and X are as defined above,
is required, 2 moles of the compound VI per mole of the compound VII are preferably employed.

The resulting compounds of formula I may be isolated and purified using conventional techniques. Where required, free base forms of the compounds may be converted into acid addition salt forms in conventional manner, or vice versa.

The compounds of formulae VI and VII are either known or may be produced in conventional manner from available materials.

When $R_1$ signifies a radical of formula II, n and m preferably each signifies 2. When Y signifies an N-alkyl group, optionally hydroxy-substituted, it preferably signifies an N-alkyl or N-monohydroxyalkyl group of 1 or 2 carbon atoms. Preferably, Y signifies a direct bond, an N-alykl radical, optionally hydroxy-substituted, or a radical of formula III or IV, more preferably a direct bond or a radical of formula III or IV.

When $R_1$ signifies a radical of formula V, p preferably signifies 2.

X preferably signifies oxygen or sulphur.

The compounds of formula I are useful because they possess chemotherapeutic activity. In particular, they are useful in the treatment of helminthiasis, in particular trematodiasis, more particularly schistosomiasis, as indicated in in vivo tests in the mouse and hamster, in a dosage range of from 5 to 250 mg/kg of animal body weight administered daily on 5 consecutive days, orally and/or parenterally. The experimental methods employed correspond to those of J. Pellegrino and Naftale Katz, Advances in Parasitology 6, 233–290 (1968) and Duvall R. H. and De Witt, W. B., Am J. Trop. Med Hyg. 16, 483–486 (1967). Albino mice and hamsters, inoculated subcutaneously with 100 ± 10, or 60 ± 10 cercariae of Schistosoma mansoni (Liberia-strain) may be employed as test animals.

The compounds are also useful in the treatment of protozoal disorders, e.g. amoebiasis, trichomoniasis and coccidiosis. Their activity against amoeba and trichomonads is indicated in vitro by determination of the minimum lethal concentration in the series dilution test after 48 hours incubation at 37° C. The anti-trichomonad activity is determined by addition of the test substance to a T. Vaginalis culture in a CACH medium [Müller et.al., Angew. Parasit. 11, 170 (1970)] at concentrations of about 0.02 to 0.1 μg/ml. The amoebicidal activity is determined in a TTY-SB medium against monoxenically cultivated E. histolytica amoeba [Diamond, L. S., J. Parasit. 54, 715 (1968) at concentrations of about 0.2 to 3.1 μg/ml. The anti-trichomonad activity is confirmed in vivo in the mouse at a dosage of from 100 to 300 mg/kg of animal body weight. The amoebicidal activity is also indicated in vivo in the rat and hamster at a dosage of 50 to 150 mg/kg of animal body weight administered thrice.

The anti-coccidal activity is indicated in vivo in chicks. For example, when added to feed at concentrations of, for example, about 80 p.p.m., the compounds inhibit the course of infection of blind gut coccidiosis in chicks.

For the above-mentioned uses, the dosage administered will, of course, vary depending on the compound employed, mode of administration and treatment desired. However, for the treatment of schistosomiasis, amoebiasis and trichomoniasis, in general, satisfactory results are obtained when administered at a daily dosage of, respectively, from about 5 to 250 mg/kg, 5 to 150 mg/kg and 5 to 300 mg/kg and to mg/kg of animal body weight, conveniently given in divided dosages two to four times daily, or in sustained release form. For the larger mammals, the corresponding total daily dosages are in the range, respectively, of 500 to 5000 mg, 400 to 3000 mg, 250 to 700 mg, respectively, and dosage forms suitable for oral administration comprise from about 125 to 2500 mg 100 to 1500 mg and 62.5 to 350 mg, respectively. For use in the treatment of coccidiosis in animals, the compounds are suitably added to animal food or drink as required, for example to food at a concentration of 80 ppm.

The preferred compounds against coccidiosis, schistosomiasis, and trichomoniasis and amoebiasis are, respectively, 1-(5-nitrothiazolyl-2)-3-[(4-methyl)-piperazino-(1)-methyl]imidazolidinthione-(2), 1-(5-nitrothiazolyl-2)-3-(3-carboxypropyl)-aminomethylimidazolidinthione-(2), and 1-(5-nitrothiazolyl-2)-3-[(4-hydroxyethyl)-piperazino-(1)-methyl]-limidazolidinthione-(2).

The compounds of formula I also possess inhibiting activity against bacteria, and are therefore useful as bacterial growth inhibitors, as indicated in vitro in the series dilution test at concentrations of from about 1.25 to 50 μg/ml and in vivo in the mouse at dosages of from about 30 to about 200 mg/kg of animal body weight, administered orally or sub-cutaneously, against a variety of bacterial strains, for example Staph. Aureus, E. coli, Shigella flexneri, Klebsiella pneumoniae and Salmonella.

For thus usage, the dosage to be administered will, of course, vary depending on the compound employed, mode of administration and treatment desired. However, in general, satisfactory results are obtained when administered at a daily dosage of from about 30 to about 200 mg/kg of animal body weight, conveniently given in divided doses two to four times daily, or in sustained release form. For the larger mammals, the daily dosage is from about 2 to 5 g, and dosage forms suitable for oral administration comprise from about 500 mg to 2.5 g.

For this usage, the preferred compounds are 1-(5-nitrothiazolyl-2)-3-pyrrolidinomethylimidazolidinthione-(2) and 1-(5-nitrothiazolyl-2)-3-[(4-hydroxyethyl)-piperazino-(1)-methyl]limidazolidinone-(2).

The compounds may be admixed with conventional chemotherapeutically acceptable diluents and carriers, and administered in such forms as tablets, capsules or injectable solutions.

The compounds may be used in free base form or in the form of their chemotherapeutically acceptable acid addition salts, which salt forms have the same order of activity as the free base forms.

The following Examples, in which all temperatures are in ° C, illustrate the invention.

EXAMPLE 1:

1-(5-Nitrothiazolyl-2)-3-pyrrolidinomethylimidazolidinone-(2)

To a solution of 2.31 g of pyrrolidine in 75 ml of dried dioxane, is added 0.99 g of paraformaldehyde and the mixture is maintained at 40° for 30 minutes. 6.42 g of 1-(5-nitrothiazolyl-2)-imidazolidinone-(2) is then added and the mixture maintained at 40° for 24 hours. The solvent is then distilled off and residue is divided between benzene/water. The benzene phase is washed with water and evaporated to dryness to obtain the heading compound, m.p. 146° to 148°, as residue.

In manner analogous to Example 1, employing appropriate starting materials in approximately equivalent amounts, the following compounds (Examples 2 to 16) may be obtained:

2. 1-(5-nitrothiazolyl-2)-3-pyrrolidinemethylimidazolidinthione-(2), m.p. 151°–153°,
3. 1-(5-nitrothiazolyl-2)-3-[(4-hydroxyethyl)piperazino-(1)-methyl]imidazolidinone-(2), m.p. 130°–134°,
4. 1-5-nitrothiazolyl-2)-3-[(4-hydroxyethyl)piperazino-(1)-methyl]imidazolidinthione-(2), m.p. 173°–175°,
5. 1,4-bis[1-(5-nitrothiazolyl-2)-2-oxoimidazolidino-(3)-methyl]piperazine, m.p. 229°–232°,
6. 1,4-bis[1-(5-nitrothiazolyl-2)-2-thioimidazolidino-(3)-methyl]piperazine, m.p. 248°–250°,
7. 1-(5-nitrothiazolyl-2)-3-[4-hydroxymethylphenyl)-piperazino-(1)]methylimidazolidinone-(2), m.p. 116°–117°,
8. 1-(5-nitrothiazolyl-2)-3-[4-(3-chloro-4-hydroxymethylphenyl)piperazino-(1)]methylimidazolidinthione-(2), m.p. 174°–175°,
9. 1-(5-nitrothiazolyl-2)-3-(3-carboxypropyl)aminomethylimidazolidinthione-(2), m.p. 106° (decomp.),
10. 1-(5-nitrothiazolyl-2)-3-(4-methylpiperazino-1)-methylimidazolidinthione-(2), m.p. 182°, 11,12. 1-(5-nitrothiazolyl-2)-3-[4-(3-chloro-4-formylphenyl)piperazino-(1)]-methylimidazolidinone-(2) or -thione-(2), 13,14. 1-(5-nitrothiazolyl-2)-3-[(4-carboxy-4-aminobutyl)aminomethyl]-imidazolidinone-(2) or -thione-(2), 15. 1-(5-nitrothiazolyl-2)-3-(N-piperidino)methyl-2-iminoimidazoline, and 16. 1-(5-nitrothiazolyl-2)-3-(N-hexahydroazepino)methyl-2-iminoimidazoline.

We claim:

1. A compound of formula I,

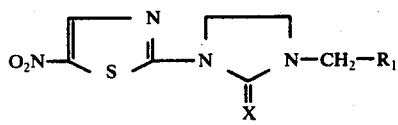

I in which
X is oxygen, sulphur or imino, and
R₁ is

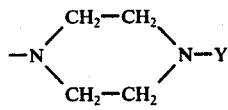

wherein y is alkyl of 1 to 4 carbon atoms or monohydroxy alkyl of 1 to 4 carbon atoms, or chemotherapeutically acceptable acid additiion salts thereof.

2. Compounds of claim 1, in which X is oxygen or sulphur.

3. The compound of claim 1, which is 1-(5-nitrothiazolyl-2)-3-[(4-methyl)piperazino-(1)-methyl]-imidazolinthione-(2).

4. The compound of claim 1, which is 1-(5-nitrothiazolyl-2)-3-[(4-hydroxyethyl)piperazino-(1)-methyl]-imidazolidinthione-(2).

5. The compound of claim 1, which is 1-(5-nitrothiazolyl-2)-3-[(4-hydroxyethyl)piperazino-(2)-methyl]-imidazolidinone-(2).

6. A chemotherapeutic composition consisting essentially of a compoound of claim 1 in association with a chemotherapeutically acceptable diluent or carrier.

7. A method of treating schistosomiasis, trichomoiasis or coccidiosis or of inhibiting bacterial growth, consisting essentially of administering to a subject in need of such treatment an effective amount of a compound of claim 1.

8. A pharmaceutical composition according to claim 6 in which the compound is 1-(5-nitrothiazolyl-2)-3-[(4-hydroxyethyl)piperazino-(1)-methyl]imidazolidinone-(2).

9. A method according to claim 7 in which the compound is 1-(5-nitrothiazolyl-2)-3-](4-hydroxyethyl)-piperazino-(1)-methyl]imidazolidinone-(2).

* * * * *